(12) United States Patent
Dennett, Jr. et al.

(10) Patent No.: US 7,291,324 B2
(45) Date of Patent: Nov. 6, 2007

(54) METHOD OF BOWEL CLEANSING

(75) Inventors: Edmund V. Dennett, Jr., Walpole, MA (US); Robert M Raleigh, Braintree, MA (US); Mark V B Cleveland, Duxbury, MA (US); Russell W Pelham, Duxbury, MA (US)

(73) Assignee: Braintree Laboratories Inc., Braintree, MA (US)

( * ) Notice: Subject to any disclaimer, the term of this patent is extended or adjusted under 35 U.S.C. 154(b) by 0 days.

(21) Appl. No.: 10/277,620

(22) Filed: Oct. 22, 2002

(65) Prior Publication Data
US 2004/0191213 A1 Sep. 30, 2004

(51) Int. Cl.
*A61K 31/74* (2006.01)
*A61K 9/00* (2006.01)

(52) U.S. Cl. .................... 424/78.01; 424/400; 514/892

(58) Field of Classification Search ................ 424/400, 424/439, 78.01; 514/892
See application file for complete search history.

(56) References Cited

U.S. PATENT DOCUMENTS

| | | | |
|---|---|---|---|
| 5,197,950 A * | 3/1993 | Clayton | ........................ 604/28 |
| 5,616,346 A | 4/1997 | Aronchick | |
| 5,670,158 A * | 9/1997 | Davis et al. | ................ 424/400 |
| 5,710,183 A | 1/1998 | Halow | |
| 5,997,906 A | 12/1999 | Wood et al. | |
| 6,162,464 A | 12/2000 | Jacob et al. | |

OTHER PUBLICATIONS

Brady et al. Effect of Bisacodyl on Gut Lavage Cleansing for Colonoscopy (1987; 19:34-38; Gastroenterology Service and General Surgery Dept, Wilford Hall USAF Medical Center, San Antonio, Texas, USA).*
Adams et al., Bisacodyl Reduces the Volume or Polyethylene Glycol Solution Required for Bowel Preparation (1994; 37:229-234; Colorectal Unit, St George Hospital, Sydney, Australia).*
Grundel et al., Improvements in Mechanical Bowel Preparation for Elective Colorectal Surgery (Dis Colon Rectum 1997; 40:1348-1352).*
1998 (52nd edition) Physician Desk Reference at p. 1810 for DULCOLAX.*
W. Adams, et al., "Bisacodyl Reduces the Volume of Polyethylene Glyco Solution Required for Bowel Preparation", Colorectal Unit, Sst. George Hospital, Sydney, Australia, Dis Colon Rectum, Mar. 1994. p. 229-235.
B. Bokemeyer, "Koloskopievorbereitung", Verdauungskrankheiten, 18: 17-24, 2000.
C.E. Brady, et al., "Effect of Bisacodyl on Gut Lavage Cleansing for Colonoscopy", Analysis of Clinical Reseach, Analysis of Clinical Research 19:34-38, 1987.
W.K. Clarkston and O.J.Smith, "The Use of GoLYTELY and Dulcolax in Combination in Outpatient Colonoscopy", J. Clinical Gastronenterology 17(2):146-8, 1993.
G.R. Davis, et al., "Development of a Lavage Solution Associated with Minimal Water and Electrolyte Absorption or Secretion", Gastroenterology May 1980:78,991-995.

K. Grundel,et al., "Improvements in Mechanical Bowel Preparation for Elective Colorectal Surgery", Dis Colon Rectum, Nov. 1997:40(11) :1348-1352.
E. Lind and J.N. Wiig, "Peroral emptying of the colon. A randomized comparison of 4 and 1.5 liter regimens", Tidssky Nor Laegenforen, 110(11):1357-8, 1990.
V.K.Sharma, et al., Prospective, randomized, controlled comparison of the use of polyethylene glycol electrolyte lavage solution in four-liter versus two-liter volumes and pretreatment with either magnesium citrate or bisacodyl for colonoscopy preparation, Gastrointestinal Endoscopy 1998,47:2:167-171.
M.Vilien and M.Rytkonen, "Golytely Preparation for Colonoscopy: 1.5 Liters is Enough for Outpatients", Endoscopy 22:168-170, 1990.
"Safety of Sodium Phosphates Oral Solutions" Sep. 17, 2001, Food and Drug Administration Science Background, U.S. Food & Drug Administration, Center for Drug Evaluation and Research. Web address: http;//www.fda.gov/cder/drug/safety/sodiumphosphate.htm.
InKine Pharmaceutical Company, Inc. package insert 2000, Visicol Tablets.
Prescribing information from Fleet "Fleet Phospho-soda OTC, An oral saline laxative", Web address: http//www.phosphosoda.com/HCP/HCPPDR.asp, Feb. 18, 2003.
Ziegenhagen, et al., "Senna vs. Bisacodyl in Addition to Golytely Lavage for Colonoscopy Preparation—a Prospective Randomixed Trial," Z Gastroenterol, (1992), pp. 17-19, vol. 30.
Toledo, et al., "Review Article: Colon Cleansing Preparation for Gastrointestinal Procedures," *Aliment Pharmacol Ther*, (2001), pp. 605-611, vol. 15.
Description of Clinical Trials, Jul. 2002.
Chan, et al., "Use of Oral Sodium Phosphate Colonic Lavage Solution by Canadian Colonscopists: Pitfalls and Complications", *Canadian Journal of Gastroenterology*, vol. 11(4), pp. 334-338 (1997).
Ahmed, et al., "Oral Sodium Phosphate Catharsis and Acute Renal Failure", *American Journal of Gastroenterology*, vol. 91(6), pp. 1261-1262 (1996).
DiPalma, et al., "Biochemical Effects of Oral Sodium Phosphate", *Digestive Diseases and Sciences*, vol. 41(4), pp. 749-753 (1996).
Kolts, et al., "A Comparison of the Effectiveness and Patient Tolerance of Oral Sodium Phosphate, Castor Oil, and Standard Electrolyte Lavage for Colonoscopy or Sigmoidoscopy Preparation", *American Journal of Gastroenterology*, vol. 88(8), pp. 1218-1223 (1993).
Vanner, et al., "A Randomized Prospective Trial Comparing Oral Sodium Phosphate with Standard Polyethylene glycol-based lavage solution (Golytely) in the Preparation of Patients for Colonoscopy", *American Journal of Gastroenterology*, vol. 85(4), pp. 422-427 (1990).

* cited by examiner

*Primary Examiner*—Michael G. Hartley
*Assistant Examiner*—Blessing Fubara
(74) *Attorney, Agent, or Firm*—Wilmer Cutler Pickering Hale and Dorr LLP

(57) ABSTRACT

Stimulant laxative in combination with an osmotic laxative produces safe and effective bowel and colon cleansing with a reduced volume of liquid input. Administering to a patient an oral stimulant laxative, such as bisacodyl, followed, after a biologically determined interval, by a reduced volume of a PEG in water solution cleanses the bowels and colon in preparation for diagnostic colonoscopy, without the profuse uncontrollable diarrhea that typically follows either ingestion of large volume isotonic ravages, or smaller volume hypertonic lavages.

4 Claims, No Drawings

METHOD OF BOWEL CLEANSING

BACKGROUND OF THE INVENTION

1. Field of the Invention

We have now discovered a new method that can be used to safely and effectively cleanse a patient's bowels, especially the colon prior to diagnostic or surgical procedures.

2. Background Information

Although years of clinical research have been expended to make early detection of colorectal cancer (CRC) a high clinical priority, the disease remains the second leading cause of cancer-related death in the United States. In 1999, an estimated 60,000 deaths were attributed to CRC which accounted for the third highest number of new cancer cases that year, only lagging prostate and respiratory cancers for men and breast and respiratory cancers in women. Investigators estimate there were 129,000 new cases in 1999 alone. Lifetime risk for developing CRC is therefore 1 case per 18 people in the United States.

Despite the success of screening procedures which can reduce the rate of death by detecting early cancer or premalignant polyps, only about 30% of eligible patients are screened. Reasons given for this low rate of screening include physicians', patients' and health care providers' reluctance to encourage, receive, or pay for these procedures. This has been recognized most recently at the Federal level on Jul. 10, 2002 when a U.S. Senate committee voted to require all private health insurance plans in the United States to provide coverage for colonoscopies and other tests to detect colon cancer in people who are 50 or older or have a high risk of developing the disease.

Patients who are undergoing surgical procedures or diagnostic examinations of the large bowel usually undergo preparation to assure that the bowel is cleansed of all fecal material adequately before the procedure. This serves to minimize contaminating the operating area for example, during surgery for explorations of potential masses or for bowel resection. An additional purpose is to allow a clean interior surface of the colon for diagnostic examination, for example during endoscopic surveillance as a diagnostic examination for detecting colon cancer.

In sigmoidoscopy, colonoscopy, radiographic examination, preparation for patients undergoing bowel surgery, and other medical or diagnostic procedures on the bowels or colon, it is important that the bowels and colon be thoroughly purged and cleaned. In particular, it is essential that as much fecal matter as possible be removed from the colon to permit adequate visualization of the intestinal mucosa. This is important prior to, for example, diagnostic procedures such as flexible sigmoidoscopy or colonoscopy, diagnostic examinations widely performed to screen patients for diseases of the colon. In addition, it is important that the intestines be cleansed thoroughly in order to obtain satisfactory radiographs of the colon. The same condition also applies when the colon is preoperatively prepared for surgery, where removal of fecal waste materials is critically important for patient safety.

Among the procedures for CRC detection, controversy over which is the most cost effective continues, but most practitioners today agree that colonoscopy detects the highest rate of cancers and affords simultaneously the opportunity for their endoscopic removal. To prepare the colon for endoscopic exam, current cleaning procedures include the combination of reduced food intake with laxatives, enemas, suppositories, bowel evacuants, or orthograde colonic lavage. Orthograde lavage with Polyethylene Glycol/Electrolyte Solutions (PEG-ELS, GoLYTELY® or SF-ELS, NuLYTELY®) is a frequently prescribed preparation. These "preps", consisting of 4 L of solution, are generally uncomfortable for the patient to complete. They often complain of a sense of fullness, nausea, cramping, and vomiting, sometimes of such magnitude that they do not complete the prescribed regimen. Failure to complete the regimen is a frequently named cause of inadequate bowel cleansing which often results in termination of the colonoscopy. One way to improve the patients' willingness to undergo and complete colonoscopy would be to reduce the volume of lavage solution.

Physicians and surgeons have developed a variety of means to achieve the desired level of colon cleansing. The use of dietary restrictions, laxatives, enemas, and whole-bowel lavage solutions, alone or together, has been employed. Two components of this bowel-cleansing procedure, namely, a clean colon to assist the medical procedure, and safe, easy to take and pleasant "patient friendly" colon-cleaning procedure, have not been simultaneously attainable in present medical practice. What the physician may find to provide the "cleanest" colon may require multiple days of fasting, laxative use and large volume liquid ingestion by the patient. What the patient perceives as the most comfortable preparation regimen may not yield an adequately cleansed colon. In many cases, patients do not comply with preparation regimens that the patients feel are too inconvenient or too uncomfortable. In addition, many preparations may pose a health risk, as they cause fluid and electrolyte disturbances in the body, which are known to be harmful, even deadly, in some patients. The variety of methods now used for colonic evacuation is a testament to the lack of an ideal means to achieve its goals. What is needed is a procedure that is both highly efficacious and safe, while at the same time is tolerable to the patient, to encourage compliance for frequent examinations.

Large volume orally administered compositions have been developed for use as gastrointestinal washes for diagnostic purposes or for use as cathartic laxatives. Such orally administered preparations are usually formulated as dilute or isotonic solutions of electrolytes such as sodium sulfate, sodium bicarbonate, sodium chloride and potassium chloride. These orally administered compositions are useful in the rapid cleansing of the colon for diagnostic purposes. These formulations may include other agents such as polyethylene glycol. These formulations have generally been administered in a quantity of about four liters as isotonic solutions. One example composition is GoLYTELY® formulated, in one liter of water, according to the following: polyethylene glycol 59 g, sodium sulfate 5.68 g, sodium bicarbonate 1.69 g, sodium chloride 1.46 g, potassium chloride 0.745 g (Davis et al. Gastroenterology 1980; 78: 991-995).

Commercially available products embodying these formulations sometimes utilize polyethylene glycol, a non-absorbable osmotic agent, with an isotonic mixture of electrolytes for replenishment, so that patients do not become dehydrated or experience clinically significant electrolyte shifts. Because the solutions are isotonic, patients are required to ingest a significant amount of volume of these solutions, up to one eight ounce glass every ten minutes for a total of one gallon of fluid, to achieve effective purging.

The large volume required for effective use of this type of formulation for lavage is frequently associated with distention, nausea, cramping, vomiting, and significant patient discomfort. Thus, while these formulations are generally effective, they are not well tolerated. Without close supervision, many patients do not take the complete course of preparation.

Sodium sulfate and phosphate salts have been used as laxatives when diluted in a small volume (~300 ml) concentrated solution and taken in tablespoon sized (15 ml) daily doses. An example of this use is Glauber's Salt's (containing sodium sulfate). However, because of their small volumes, when used in this fashion they do not sufficiently clean the colon for diagnostic or surgical procedures. Also these small volume preparations do not contain polyethylene glycol. Sodium sulfate combined with polyethylene glycol and various other salts, administered in large volumes (1 gallon) over a short period of time is an effective gastrointestinal lavage, which cleanses the colon prior to colonoscopy or surgical procedures as described above.

Another drawback of these prior art preparations is their unpleasant, bitter, saline taste. This can promote nausea and vomiting in sensitive patients—thereby preventing ingestion. It is difficult to overcome this unpleasant taste, even the most common natural sweeteners such as glucose, fructose, saccharose, and sorbitol could change the osmolarity of these orally administered solutions resulting in potentially dangerous electrolyte imbalances.

In an attempt to avoid the problems associated with the high volume types of preparations, other investigators have utilized ingestible preparations that consist of aqueous solutions of concentrated phosphate salts. The aqueous phosphate salt concentrate produces a tremendous osmotic effect on the intra-luminal contents of the bowel and therefore, evacuation of the bowel occurs with a large influx of water and electrolytes into the colon from the body. These phosphate salt preparations have been developed for the purpose of decreasing the volume required in colonic purgations. One such preparation basically is comprised of 480 grams per liter monobasic sodium phosphate and 180 grams per liter dibasic sodium phosphate in stabilized buffered aqueous solution and is sold under the brand name Fleets Phospho-Soda®. Patients are typically required to take two (2) three ounce doses of this preparation, separated by a three to 12 hour interval for a total of six ounces (180 ml), which is a significant reduction compared to the large 1 gallon volumes required by the high volume preparations. Additionally, non-aqueous tablet or capsule formulations of sodium phosphates and sulfates have been used (U.S. Pat. Nos. 5,997,906, 6,162,464, and 5,616,346).

These small volume sulfate/phosphate solutions and non-aqueous formulations have been shown to cause massive electrolyte and fluid shifts that are clinically significant to the patient (US Food and Drug Administration, Center for Drug Evaluation and Research, Sep. 17, 2001; 2002 Physician's Desk Reference, prescribing information for Fleet's Phospho Soda and InKine Pharmaceutical's Visicol®). The terms "clinically significant" as used herein are meant to convey alterations in blood chemistry that are outside the normal upper or lower limits of their normal range or other untoward effects. These solutions are hyperosmotic; that is the electrolyte concentration of the solution is much higher than the electrolyte concentration in the human body. Available products, as Fleet's Phospho-Soda, and the solid dosage form such as Visicol tablets (sodium phosphate salts) are examples of small volume electrolyte preparations. All of these products have been seen to cause clinically significant electrolyte disturbances and fluid shifts, and disturbances in cardiac and renal function when administered to patients (US Food and Drug Administration, Center for Drug Evaluation and Research, Sep. 17, 2001).

To overcome the risks and electrolyte disturbances that occur with the small volume laxative preparations, large volume "lavage" solutions were developed to be isotonic. Preparing a patient for a surgical or diagnostic procedure on the colon with such an isotonic lavage would result in only minimal fluid and electrolyte shifts in the patient. GOLYTELY®, NULYTELY®, and CoLyte® are examples of such large volume lavages. Because these lavages are isotonic, the patient experiences minimal, non-clinically significant fluid and electrolyte shifts, if any, upon their administration.

Davis and Fordtran (Gastroenterology 78:991-5, 1980) developed a four-liter polyethylene glycol and electrolyte bowel lavage solution (GoLYTELY), which has been shown to be safe and effective as a means of rapidly evacuating the colon in preparation for colonoscopy, barium enema and surgery. When ingested it produces a voluminous, liquid stool with minimal changes in the patient's water and electrolyte balance. As such, lavage solutions are often referred to as the "gold standard" by physicians who wish their patients to achieve the cleanest colon. Although, the formula for this drug was modified to improve the flavor of the solution, many patients have expressed a dislike for the large volumes that must be ingested. Indeed, many of the labeled adverse reactions typical of this kind of preparation (such as nausea and vomiting) can be attributed to a volume effect. Ideally, one would want to somehow reduce the dose, thereby increasing patient comfort, without compromising the quality of bowel cleansing.

Clinical studies spanning over 20 years have attempted to reduce the volume of PEG based lavage preparations by combining them with laxatives, most notably bisacodyl. In many of these initial attempts, the volume of the solution was maintained at 4L, even with the addition of bisacodyl. In other experiments, attempts were made to use smaller volumes of a PEG based solution without bisacodyl or a laxative. Generally, these attempts produced improved patient symptoms but reduced the quality of the colonoscopy below acceptable standards. Vilien and Rytkonen (Endoscopy 22:168-170, 1999) published a study of 50 patients that compared a reduced volume GoLYTELY regimen with their standard GoLYTELY preparation for colonoscopy. Colonoscopists who were unaware of the cleansing regimen that the patients had received rated the cleansing efficacy. On the day before examination, all patients were given 10 mg bisacodyl followed by a liquid diet. Then, on the morning of the exam, patients drank either 1.5 or 3 liters of GoLYTELY (depending upon the randomization schedule). The authors concluded that there was less complete cleansing when the lower lavage volume was used. However, it is not clear how well these two treatments cleansed the bowel in comparison to the standard 4 liters of lavage solution alone.

Other authors have tried to combine colon-cleansing modalities to achieve a clean, well-tolerated, preparation. Adams et al. (Dis. Colon Rectum 37:229-234, 1994) compared preparation with bisacodyl followed eight hours later by 2 liters of GoLYTELY to the "standard" four liters of GoLYTELY. These authors found that when patients received the bisacodyl 28-30 hours before examination and were placed on a clear liquid diet for more than 30 hours before examination, the quality of bowel cleansing between the two preparations appeared to be equivalent but the bisacodyl plus 2 liters GoLYTELY method was better tolerated. However, patients who received the bisacodyl plus 2 liters of GoLYTELY, but were not restricted to liquids for more than 30 hours before examination, did not have satisfactory preparation.

In a similar study, of patients scheduled for colon surgery, the results of colon cleansing were judged to be of the same visual quality, but the patients did not find any improvement in their level of discomfort (Grundel K, Schwenk W., Bohm B, and Muller J M, Dis Colon Rectum 1997 Nov; 40(11): 1348-52).

Other studies have failed to find a good combination of physician and patient assessments when a laxative is used in conjunction with a reduced lavage volume. Indeed, Bokemeyer (Verdauungskrankheiten, 18:17-24, 2000) found that the laxative plus reduced lavage volume resulted in "Colonoscopy preparation with a smaller volume of PEG-lavage solution in combination with a laxative (X-Prep) produced significantly worse results." See also the work of Lind and Wiig (Tidsskr Nor Laegeforen 110:1357-1358, 1990) and of Brady and others (Ann Clin Research 19:34-38, 1987) for other failed attempts.

An alternative approach, the dosing of the patient with a laxative after the administration of a lavage has been tried and found to produce no improvement in patient symptoms over administering the full lavage volume (Clarkston and Smith J. Clin Gastroenterology 17:146-148, 1993).

Finally, the simultaneous co-administration of laxatives with a reduced volume of PEG-ELS produced cleansing similar to 4L of PEG-ELS alone and reduced patient symptoms, but, the patients were also pretreated with simethicone, an anti-gas medication (Sharma et al., Gastrointestinal Endoscopy, 47(2):167-71, 1998).

Thus, despite others' attempts, improved patient symptoms do not necessarily follow the use of reduced volumes of lavage fluids with laxative pretreatment. Nor does the combination reliably produce a colon preparation that is as good as that achieved when a large volume lavage solution is used.

Furthermore, the attempts to cleanse the colon with a smaller volume of a lavage solution in combination with a laxative have made the patients and physicians engage in protracted fasting and a cumbersome schedule for the preparation. For example, Grundel et al required their patients to consume clear liquids and soup for two days before the surgery, so it is perhaps not surprising that they achieved good colon clean-out with a minimal volume lavage. Adams required patients consume only clear liquids for 28-32 hours before examination.

As noted above, what we have found is that prior attempts to obtain at the same time both an adequate preparation and improved patient comfort have failed because they overlooked key parameters in the dosing of the patients, namely, the duration of time between laxative and lavage ingestion and the effect of the laxative prior to the lavage. Adams required patients consume only clear liquids for 28-30 hours before examination.

From the foregoing, it can be seen that the two approaches to colonic lavage that have been used in the past have significant drawbacks that have not been resolved by prior attempts. The isotonic solutions, while not causing clinically significant fluid or electrolyte shifts, are, of necessity, of large volume, and difficult for patient ingestion. The hypertonic solutions or concentrated non-aqueous formulations are sometimes inadequate to prepare the colon and more importantly, can cause clinically significant electrolyte and fluid shifts, which have been known to cause deaths. Thus, it is desirable to have a small volume orally administered colonic purgative formulation which may be easily and conveniently administered and which avoids the clinically significant problems and objectionable tastes of known formulations. It can also be seen that it is desirable to have such a purgative formulation which may be administered without the large volumes necessary in conventional formulations and which avoids other potentially irritant chemicals or chemicals which could effect osmolarity. In the nearly 20 years since the advent of large volume colonic lavage solutions, there has not been success in discovering an effective small volume gastrointestinal cleansing preparation that minimized fluid or electrolyte shifts. Concentrating the large volume lavages into smaller volumes does not achieve the same effectiveness, and is not as safe. This is because the components are not soluble in the small volumes necessary and because the concentrations are such that dangerous electrolyte shifts could occur. One purpose of the present research was to develop a safe, effective, and well tolerated method of cleansing a colon that required a small volume of solution.

Available methods for cleansing a colon are not optimally tolerated by patients, and have potentially dangerous side effects. We have now found that administering a reduced volume of a solution containing an osmotic laxative, such as polyethylene glycol in conjunction with a stimulant laxative, can achieve safe and effective cleansing of the colon prior to diagnostic or surgical procedures.

SUMMARY OF THE INVENTION

We have now discovered that administering a stimulant laxative in combination with an osmotic laxative produces safe and effective colon cleansing with a reduced volume of liquid input.

We have now seen that a colon can be adequately cleansed for a diagnostic or surgical procedure by first administering a stimulant laxative, such as bisacodyl, in an amount sufficient to produce a bowel movement to the patient, then allowing the stimulant laxative to produce the bowel movement, and following this bowel movement orally administering a reduced volume of an osmotic laxative to the patient.

Using this protocol, we have seen that patients can achieve adequate cleansing with ingestion of only 2 liters of a PEG in water solution after a bowel movement produced by the stimulant laxative.

We have seen that this regimen results in adequate preparation of the colon for examination or surgery with reduced occurrence of symptoms such as discomfort, nausea, or vomiting.

The regimen produces bowel cleaning that is equivalent to the standard 4L preparations, but yields improved cleansing compared to other 2L preparations. Also, this regimen reduced patient symptoms and reduced preparation time compared to both 4L and other 2L preparations.

DETAILED DESCRIPTION OF AN ILLUSTRATIVE EMBODIMENT

It has been determined, surprisingly, that a specific regimen of a stimulant laxative, such as bisacodyl, which precedes by a biologically-defined interval the consumption of a reduced volume of an orthograde lavage solution, produces a superior combination of bowel cleanliness (as judged by the physician), a reduced regimen preparation time and an improved patient acceptance of the procedure. This regimen of laxative and lavage produces results that are superior and different from either laxative or reduced volume lavage alone, or what might be expected from their combination in a purely additive manner, or that would be expected if the specific regimen is not followed. Furthermore, this method permits the use of a lower volume of the lavage solution than if it were to be used alone. Additionally, this regimen results in reduced occurrence of most common symptoms complained of by patients. Finally, it has been discovered that this dual modality treatment is most advantageous if the timing of its two components is properly controlled. This finding is highly unexpected in that the adoption of this dosing regimen has not been previously appreciated in the art.

This finding occurred in the course of developing an improved lavage-laxative regimen for use in colonoscopy. As such, the results are pertinent to any situation in which a physician or surgeon requires a clean bowel in a patient.

It has been believed that profuse, uncontrolled diarrhea was necessary to produce adequate cleansing of the colon. We have now seen that safe and effective cleansing of the colon can occur without the ingestion of large volumes of lavage solutions, without the unpleasant, bitter, and dangerous hypertonic salt solutions.

Stimulant laxatives cause rhythmic muscle contractions in the large intestines. Effective doses of stimulant laxatives include: Aloe, 250-1000 mg.; Bisacodyl, about 5-80 mg.; Casanthranol, 30 to 360 mg.; Cascara aromatic fluid extract, 2-24 ml.; Cascara sagrada bark, 300-4000 mg.; Cascada sagrada extract, 300 to 2000 mg.; Cascara sagrada fliuid extract, 0.5 to 5 ml.; Castor oil, 15-240 ml.; Danthron, 75-300 mg.; Dehydrocholic Acid, 250-2000 mg; Phenolphthalein, 30-1000 mg.; Sennosides A and B, 12-200 mg.; and Picosulfate, 1-100 mg. Stimulant laxatives sometimes produce cramping, gas, diarrhea and may be habit forming. Of course, larger or smaller doses may be used, as necessary, to produce a bowel movement within less than about 12 hours, while avoiding unnecessary discomfort.

Bisacodyl is a stimulant laxative, available without prescription, used to treat constipation. Bisacodyl is available in tablets, suppositories, and in premixed enema formulations. Bisacodyl enemas are usually effective to produce a bowel movement in about 20 minutes, suppositories usually produce a bowel movement in about an hour, and oral administration of a tablet usually results in a bowel movement in about 3 to 6 hours. Bisacodyl works by stimulating the intestines and rectum to produce a bowel movement. Stimulant laxatives, alone, can be effective to treat constipation, but have not been effective to cleanse satisfactorily a patients colon prior to colonoscopic examination or surgical procedure.

Oral administration of about 5 to about 40 mg. of bisacodyl is usually effective to produce a bowel movement within about 3 to about 6 hours after administration. About 5 to about 80 mg. of bisacodyl may be administered to a patient to produce a bowel movement. Preferably, a dose of from about 10 to about 20 mg. of bisacodyl can be used. It has been shown that a 20 mg. dose of bisacodyl is effective to produce a bowel movement within reasonable time.

As shown in U.S. Pat. No. 5,710,183, Polyethylene Glycol (PEG) 3350 has been used alone as a medication to treat constipation by improving bowel motility, stool formation, or both. PEG has also been combined with soluble fiber to make a safe and effective laxative, as also shown in U.S. Pat. No. 5,710,183, and PEG can be combined with soluble fiber to improve bowel function, or to treat irritable bowel syndrome. The usual dose of PEG to treat constipation is 17 to 34 grams of PEG daily, and the greatest improvement in bowel motility is seen after a two week course of treatment. Higher doses of PEG can be used to produce one or two bowel movements within 24 hours without causing profuse diarrhea.

In one example, a package consists of 2L of NuLYTELY with 4 Bisacodyl Tablets 20 mg (5 mg each) attached to the outside of the 2-liter jug. Each dose of the NuLYTELY solution contained: Polyethylene Glycol 3350, NF, 210 g., Sodium Chloride, USP 5.60 g., Sodium Bicarbonate, USP 2.86 g., Potassium Chloride, USP 0.74 g., and optionally, 1 g. of a flavor ingredient in water to make 2L.

PEG has also been shown to be effective as a colonic purgative when large amounts of PEG are administered in large volumes of a dilute salt solution. Usually about 250 to about 400 grams of PEG are administered to the patient in about 4 liters of an electrolyte solution in water.

Oral administration of PEG can be used to produce an overnight bowel movement. The dose required will vary, but from about 10 to about 100 grams of PEG in 8 oz. of water is believed to be effective. A dose of from about 68 to about 85 grams of PEG has been shown to be effective to produce an overnight bowel movement, without profuse diarrhea. However, use of doses of less than about 200 grams of PEG have not been shown to produce adequate cleansing of the bowel.

We have now found that administering an effective amount of bisacodyl and allowing it to produce a bowel movement, followed by administering an amount of PEG solution that is substantially less than the often prescribed 4 liter "gold standard" solution, can comfortably induce colonic purgation in patients within from about 3 hours to overnight. A volume of a solution of PEG in an isotonic fluid that produces an adequately cleansed bowel is an effective amount of an osmotic laxative. Volumes from about 0.5 L to about 4L are believed to be effective. Preferably the effective volume is between about 1.5 L and about 2.5 L. Oral administration of 2 liters of isotonic solution has been effective.

Two experiments were performed. Patients undergoing routine colonoscopic examination were assigned to different treatments of bowel preparation. They were then subjected to endoscopic colonoscopy. Physicians, who were blinded to the type of preparation employed, graded the quality of the colonoscopy as "adequate" or "inadequate" based on their overall clinical impressions. In the first experiment, designated F38-13/14, ninety-three (93) patients consumed a light breakfast the day before routine colonoscopy, then took 20 mg of bisacodyl at noon after a clear liquid lunch. This was followed by 2 liters of NuLYTELY 6 hours later. In the Tables, this group receiving this combined treatment is designated "bis+6 hours +2L NuLYTELY". In a second experiment, involving seventy-eight (78) patients and designated F38-20, we again administered 20 mg of bisacodyl, as before. But this time, rather than a fixed 6 or 8 hour interval before beginning administering the lavage solution, we instructed the patients to wait for a bowel movement to occur after the laxative was taken and before starting the NuLYTELY. In the Tables, this group receiving this combined treatment is designated "bis +BM +2L NuLYTELY". As a control group, in comparison, one hundred-eighty eight (188) other patients who were treated similarly in both experiments (and whose data are herein combined for convenience) consumed a light breakfast, a clear liquid lunch, and began drinking 4 liters of NuLYTELY at 6 PM the day before their colonoscopy. In the Tables which follow, this group is designated "4L NuLYTELY". For all patients, colonoscopies were generally scheduled on the morning of the next day. In the first experiment depicted in Table 1, a 2 liter NuLYTELY® lavage solution was administered approximately 6 hours after 20 mg of the bisacodyl laxative and without regard for whether the patients had had a bowel movement after the bisacodyl. As others have shown, in this experiment, the combination of the laxative preceding the 2-liter lavage by 6 hours (the "bis+6 hours+2L NuLYTELY" group") appeared to produce fewer clinically "adequate" colonoscopy preparations as compared to when the full 4-liter lavage was employed. Although the difference was small, it is statistically and clinically significant. Even small differences in the percent of "inadequate" preparations may be clinically significant because "inadequate" preparations may result in re-preparation and thus repeated exposures to the inherent risks associated with colonoscopy.

TABLE 1

Percent Bowel Preparation Adequacy
Braintree Protocol F38-13/14
2L NuLYTELY Lavage solution administered
6 hours after 20 mg bisacodyl

| | TREATMENT | |
| --- | --- | --- |
| Rating | 4L NuLYTELY | F38-13/14 bis + 6 hours + 2L NuLYTELY |
| Adequate | 98.9% (184) | 93.5% (87) |
| Inadequate | 1.1% (4) | 6.5% (6) | p < 0.0028
() = number of patients

However, as shown in Table 1 A, when the 2L lavage was administered 6 hours after the stimulant laxative, without regard to whether the patients had had a bowel movement, no improvement in the yield of adequate preparations was observed compared with that in the prior art. Adams used a 2L PEG solution administered 8 hours after 20 mg bisacodyl, also without regard to whether the patients had had a bowel movement.

TABLE 1A

Adams: 2L PEG-ELS Lavage solution administered 8 hours after 20 mg bisacodyl.
F38-13/14: 2L NuLYTELY Lavage solution administered 6 hours after 20 mg bisacodyl.

| Rating | Adams et al | F38-13/14 bis + 6 hours + 2L NuLYTELY |
| --- | --- | --- |
| Adequate | 93.2% (166) | 93.5% (87) |
| Inadequate | 6.8% (11) | 6.5% (6) |

P = 0.903 (Adams vs. F38-13/14)

Table 2 shows that in patients who received the 2L NuLYTELY +bis preparation, where the lavage was administered 6 hours after the stimulant laxative, without regard to whether the patients had had a bowel movement, preparation-associated symptoms were not significantly reduced compared to the symptoms encountered by patients taking the 4L lavage.

TABLE 2

Bothersome to Severe Preparation Symptoms
% of Patients
Braintree Protocol F38-13/14
2L NuLYTELY Lavage solution administered
6 hours after 20 mg bisacodyl

| | TREATMENT | | |
| --- | --- | --- | --- |
| Symptom | 4L NuLYTELY | F38-13/14 bis + 6 hours + 2L NuLYTELY | p |
| Fullness | 31% (85)) | 28.2% (26) | NS |
| Cramping | 12% (33) | 12.0% (11) | NS |
| Nausea | 22% (61) | 18.3% (17) | NS |
| Vomiting | 8.8% (24) | 8.6% (8) | NS |
| Overall | 26% (71) | 23.8% (22) | NS | bis = bisacodyl
NS = not significant
() = number of patients

Again, as Table 2A shows, compared with the prior art regimen in Adams, where the 2L lavage solution was administered 8 hours after the stimulant laxative, without regard to whether the patients had had a bowel movement, there was an observed, but not in all measures, statistically significant reduction in reported symptoms associated with the preparation.

TABLE 2A

| Symptom | Adams et al | F38-13/14 bis + 6 hours + 2L NuLYTELY | P (Adams vs. F38-13/14) |
| --- | --- | --- | --- |
| Fullness/Discomfort | 35% (52) | 28.2% (26) | NS |
| Cramping/Pain | 30% (44) | 12.0% (11) | P < 0.01 |
| Nausea | 25% (37) | 18.3% (17) | NS |
| Vomiting | 6.8% (10) | 8.6% (8) | NS |
| Overall | 44% (65) | 23.8% (22) | P < 0.01 |

Adams rated symptoms such as "discomfort" on a five point scale where a score of 1 was "not uncomfortable" and a score of 5 was "unbearable" but a score of 3 was undefined. Adams et al patients who reported a "discomfort" score equal or greater than 3 were counted in Table 2A. These scores were considered equivalent to "bothersome to severe" symptom scores in the studies we conducted. For the F38-13/14 study, patients with a symptom score of 3 or greater in a given category were counted. Categories were rated on a five-point scale where a score of 1 was "None" and a score of 5 was "severe". A score of 3 was "bothersome", while a score of 4 was "distressing".

Thus, a 2 liter lavage preparation which was consumed by the patients at a fixed time interval (such as 6 or 8 hours), without regard for whether the patient had had a bowel movement in response to dose of bisacodyl, appeared to produce clinically inferior cleansing when compared to 4 L of lavage preparation without bisacodyl, and reduced the incidence of symptoms in only one out of five patient symptom categories. These results prompted us to test whether the quality of the preparation and the patient symptoms could be improved by allowing a biologically relevant event such as a bowel movement to occur after bisacodyl administration and before the administration of the lavage.

Therefore, in the next study (F38/20), we administered 20 mg of bisacodyl, but this time, rather than choose a fixed 6 or 8 hour interval before administering the lavage solution, we instructed the patients to wait for a bowel movement to occur (after the laxative was taken) before starting the NuLYTELY. This produced much improved results.

Table 3 shows that, contrary to the findings of the experiment presented in Table 1, when the low-volume lavage fluid is instituted only after the bowel movement induced by 20 mg of bisacodyl occurs, the percent of "adequate" bowel preparations increases in comparison to the results in study F-38-13/14. It is also demonstrated to be equivalent to that obtained by the "gold standard" of 4L of lavage fluid. Table 3 includes only patients who followed the clinical protocol, that is, only those patients who were compliant and waited for a bowel movement before drinking the 2L of NuLytely. (There were 14 non compliant patients, and in them 3/14 or 21% had bowel preparations that were judged by the clinicians to be "Inadequate", further supporting the value of the improved preparation.)

TABLE 3

Percent Bowel Preparation Success
Braintree Protocol F38-20
2L NuLYTELY Lavage solution administered
following a bowel movement induced by
20 mg bisacodyl

TREATMENT

| Rating | 4L NuLYTELY | F38-20 bis + BM + 2L NuLYTELY |
|---|---|---|
| Adequate | 98.9% (184) | 96.2% (75) |
| Inadequate | 1.1% (4) | 3.8% (3) | p = 0.15, no significant differences
() = number of patients

In further support of the value of the improved regimen, Table 3A compares the results we have discovered with those of the prior art. Clinically superior cleansing of the bowel can be obtained when patients are instructed to begin consuming the 2 liters of lavage solution after they have had a bowel movement following 20 mg of bisacodyl, rather than at a fixed time interval.

TABLE 3A

Comparison of Prior Art with Braintree Protocol F38-20
Percent Bowel Preparation Success
Adams: 2L PEG-ELS Lavage solution administered
8 hours after 20 mg bisacodyl
F38/20: 2L NuLYTELY Lavage solution administered
after a bowel movement following
20 mg bisacodyl

| Rating | Adams et al | F38-20 bis + BM + 2L NuLYTELY |
|---|---|---|
| Adequate | 93.2% (166) | 96.2% (75) |
| Inadequate | 6.8% (11) | 3.8% (3) |

P = 0.02675, (Adams vs. F38-20)

Table 4 shows that when this new dosage schedule is adopted, not only is the quality of the colonoscopy improved, but also, patient's symptoms and adverse events are markedly diminished. When compared to the experiment shown in Table 2, it is apparent that withholding the lavage solution until after the patient has had a complete bowel movement as a result of the laxative bisacodyl results in a nearly 50% reduction in patient discomfort in all symptom measures. Statistical significance was attained in four out of five of these symptom categories.

TABLE 4

Bothersome to Severe Preparation Symptoms
% of Patients (n)
Braintree Protocol F38-20
2L NuLYTELY Lavage solution administered following
a bowel movement induced by
20 mg bisacodyl

TREATMENT

| Symptom | 4L NuLYTELY | F38-20 bis + BM + 2L NuLYTELY | p |
|---|---|---|---|
| Fullness | 31% (85) | 16.5% (15) | <0.05 |
| Cramping | 12% (33) | 6.5% (6) | <0.03 |
| Nausea | 22% (61) | 16.2 (15) | NS |
| Vomiting | 8.8% (24) | 3.3% (3) | <0.005 |
| Overall | 26% (71) | 14.3% (13) | <0.001 |

NS = no significant differences
() = number of patients

In comparison to the prior art, the reduction in patient symptoms when a patient begins ingesting the lavage after a bowel movement produced by the action of the stimulant laxative, rather than after a fixed time interval is shown in Table 5, which compares the symptom scores for patients consuming 2 liters of lavage in F38-20. For easy comparison, the results of study F38-13/14 for bisacodyl followed 6 hours later by 2 liters of lavage, are included.

TABLE 5

Comparison of Prior Art with Braintree Protocol F38-20
% Patients with Symptoms
Adams: 2L PEG-ELS Lavage solution administered 8
hours after 20 mg bisacodyl
F38-20: 2L NuLYTELY Lavage solution administered
following a bowel movement initiated
by bisacodyl.
F38-13/14: 2L NuLYTELY Lavage solution administered
6 hours after 20 mg bisacodyl

| Symptom | Adams et al | F38-20 bis + BM + 2L NuLYTELY | P (Adams vs. F38-20) | F38-13/14 2L NuLYTELY + bis |
|---|---|---|---|---|
| Fullness/Discomfort | 35% (52) | 16.5% (15) | P < 0.05 | 28.2% (26) |
| Cramping/Pain | 30% (44) | 6.5% (6) | P < 0.05 | 12.0% (11) |
| Nausea | 25% (37) | 16.2 (15) | P < 0.05 | 18.3% (17) |
| Vomiting | 6.8% (10) | 3.3% (3) | P < 0.05 | 8.6% (8) |
| Overall | 44% (65) | 14.3% (13) | P < 0.05 | 23.8% (22) |

As in Table 2A, above, Adams et al patients who reported a symptom score such as a "discomfort" score equal or greater than 3 were counted. Adams rated symptoms on a five point scale where a score of 1 was "not uncomfortable" and a score of 5 was "unbearable" but a score of 3 was undefined. These scores were considered equivalent to "bothersome to severe" scores for the sake of Table 2A. For F38-20 and F38-13/14, patients with a symptom score of 3 or greater on the symptom categories were counted. Symptoms were rated on a five-point scale where a score of 1 was "no fullness" and a score of 5 was "severe". A score of 3 was "bothersome", while a score of 4 was "distressing".

Although the present invention has been described with reference to specific details, it is not intended that such details should be regarded as limitations upon the scope of the invention, except as and to the extent that they are included in the accompanying claims.

The advantages to the patient of this combined purgative formulation include, first avoiding the disadvantages of the large volume isotonic lavages, and the hypertonic salt solutions discussed above. Another advantage is that safe and effective colonic purgation can be achieved with a reduced duration of the preparation time in comparison to the prior art. A fourth advantage is the significant reduction in discomfort and symptoms endured by the patient.

The foregoing specification describes one embodiment of the compositions and treatment useful as a reduced volume colonic lavage, and the methods of using the same. Other stimulant laxatives are also contemplated to be useful in combination with the PEG laxative. Similarly, while PEG 3350 has been used in the examples, any PEG that is solid at room temperature may be used. In particular, PEGs with molecular weights in the range of from about 2500 to about 5000 may be used. PEGs with average molecular weights up to about 25,000 are believed to be useful. Several methods are disclosed herein of administering a subject with a compound for prevention or treatment of a particular condition. It is to be understood that in each such aspect of the invention, the invention specifically includes, also, the compound for use in the treatment or prevention of that particular condition, as well as use of the compound for the manufacture of a medicament for the treatment or prevention of that particular condition.

Similarly, while reference is typically made here in to "colon cleansing" it is understood that this invention will have value in cleansing the entire intestinal tract and rectum, from the cecum to the anus, inclusive. Additionally, the lavage solution may be packaged and stored as a kit comprising a concentrated solution of PEG and electrolyte to be reconstituted to a 2 L volume prior to administering the lavage to a patient.

The foregoing description of the illustrative embodiments reveals the general nature of the method. Others of skill in the art will appreciate that applying ordinary skill may readily modify, or adapt, the method disclosed without undue experimentation. The descriptions of the illustrative embodiments are illustrative, not limiting. The method has been described in detail for illustration. Variations to the specific details can be made by those skilled in the art.

Descriptions of a class or range useful includes a description of any subrange or subclass contained therein, as well as a separate description of each member, or value in said class.

What is claimed is:

1. A method for cleansing bowels and colon of a mammal, the method consisting essentially of:
    a) orally administering to the mammal from about 5 mg to about 40 mg of bisacodyl;
    b) waiting until the bisacodyl produces a bowel movement, the bowel movement occurring within 6 hours;
    c) orally administering to the mammal from about 50 g to about 400 g of polyethylene glycol (PEG) in from about 1.5 L to about 2.5 L of an isotonic solution following the bowel movement; and
    d) thereafter allowing the mammal to evacuate the bowels and colon;
    e) the method optionally including the further step of administering a clear liquid to the mammal after administration of the bisacodyl;
    whereby the colon is adequately cleansed to permit diagnostic testing or surgery.

2. The method of claim 1, wherein the amount of the isotonic solution is about 2 L.

3. The method of claim 1, wherein the amount of bisacodyl is from about 10 mg to about 20 mg.

4. The method of claim 1, whereby preparation time of the bowels and colon and adverse symptoms in the mammal are diminished.

* * * * *

UNITED STATES PATENT AND TRADEMARK OFFICE
CERTIFICATE OF CORRECTION

PATENT NO. : 7,291,324 B2
APPLICATION NO. : 10/277620
DATED : November 6, 2007
INVENTOR(S) : Edmund V. Dennett et al.

It is certified that error appears in the above-identified patent and that said Letters Patent is hereby corrected as shown below:

On the Title page, item [57] ABSTRACT, Section (57), should read as follows:

Stimulant laxative in combination with an osmotic laxative produces safe and effective bowel and colon cleansing with a reduced volume of liquid input. Administering to a patient an oral stimulant laxative, such as bisacodyl, followed, after a biologically determined interval, by a reduced volume of a PEG in water solution cleanses the bowels and colon in preparation for diagnostic colonoscopy, without the profuse uncontrollable diarrhea that typically follows either ingestion of large volume isotonic ~~ravages~~ lavages, or smaller volume hypertonic lavages.

Signed and Sealed this

Twenty-sixth Day of February, 2008

JON W. DUDAS
*Director of the United States Patent and Trademark Office*